(12) United States Patent
Varma et al.

(10) Patent No.: US 6,289,724 B1
(45) Date of Patent: Sep. 18, 2001

(54) METHOD AND APPARATUS FOR EXAMINING INTERNAL COMPONENTS OF A SEALED CONTAINER

(75) Inventors: Ramesh Varma, Berkeley Heights; J. Bradley Hunter, Basking Ridge; Marty Alexander, Summit, all of NJ (US)

(73) Assignee: TyCom (US) Inc., Morristown, NJ (US)

( * ) Notice: Subject to any disclaimer, the term of this patent is extended or adjusted under 35 U.S.C. 154(b) by 0 days.

(21) Appl. No.: 09/368,428

(22) Filed: Aug. 5, 1999

(51) Int. Cl.[7] .................................................. G01M 7/02
(52) U.S. Cl. .......................... 73/52; 73/12.01; 73/12.09; 73/572; 73/591
(58) Field of Search ...................... 73/572, 591, 52, 73/12.01, 12.09

(56) References Cited

U.S. PATENT DOCUMENTS 4,184,372 * 1/1980 Brown ................................. 73/572

FOREIGN PATENT DOCUMENTS

| 2189320 | * | 10/1987 | (GB) | ................ | 73/572 |
| 58-21524 | * | 2/1983 | (JP) | ................ | 73/572 |
| 59-5925 | * | 1/1984 | (JP) | ................ | 73/572 |
| 419781 | * | 11/1974 | (SU) | ................ | 73/572 |

* cited by examiner

Primary Examiner—Daniel S. Larkin

(57) ABSTRACT

A method and apparatus for examining internal components of a sealed container is disclosed. In one embodiment, the method includes the steps of attaching an acoustic sensor to an outer surface of the sealed container and moving the sealed container about at least one axis of the sealed container. An audio signal is received from the acoustic sensor, where the audio signal is generated by a component within the sealed container that is put into motion as a result of the step of moving the sealed container about the at least one axis. The audio signal is analyzed to determine the frequency of the signal. In an embodiment for an apparatus of the present invention, an acoustic sensor is attached to the sealed container. An amplifier is coupled to the acoustic sensor and receives an audio signal from the acoustic sensor. The audio signal is generated by a component within the sealed container that is put into motion as a result of movement of the sealed container. A receiver is coupled to the amplifier and receives the amplified audio signal.

19 Claims, 3 Drawing Sheets

METHOD AND APPARATUS FOR EXAMINING INTERNAL COMPONENTS OF A SEALED CONTAINER

BACKGROUND OF THE INVENTION

The present invention relates to a method and apparatus for conducting a non-destructive test on a container. More specifically, the invention provides for examining he internal components of a sealed container to determine if a component that has been previously secured in-place on a mounting structure within the sealed container has broken loose from its mounting structure.

Undersea fiber optic communication systems carry ever-increasing amounts of information. These systems are installed in-place under the oceans of the world and carry a large majority of the information that is transmitted between the world's continents. These fiber optic transmission systems remain in-place on the bottom of the ocean under thousands of fathoms, and even miles, of water for years at a time. Due to the difficulties encountered when having to repair, replace, or generally service these systems, it is desirable that these systems be highly reliable.

Long distance undersea fiber optic transmission systems include fiber optic repeaters at regular intervals that regenerate the optical signals that are received at the repeaters so that the transmitted signal does not become so attenuated during its transmission that it cannot be interpreted at the receiving station. Because these repeaters are installed under the sea and rest on the sea bottom, these repeaters must be hermetically sealed and must be formed of a rugged structure to prevent the sensitive optical components that are installed within the repeater from the environmental and other forces that may be applied to the repeater. Typically, the repeater is formed as a cylindrical container that is made from approximately one-inch thick beryllium copper. Once the internal optical components are installed within the cylinder, covers are welded onto its ends. Thus, once the cylinder is sealed, it is difficult to examine the internal components of the repeater.

Whereas the operation of the repeater may be verified by transmitting optical signals through the repeater and analyzing those optical signals, because the repeater is installed under the sea and is accessible only with great difficulty, it may be desirable to determine if there are any potential problems with the repeater that may not be discoverable by an operational analysis. One of these other potential problems could be a loose component within the repeater that, whereas the loose component has not yet affected the operation of the repeater, it could affect its operation at some point in the future; possibly at a time when the repeater is not easily accessible. An example could be a rivet or a screw that has become loose within the repeater. Whereas the loose rivet or screw may not affect the operation of the repeater when the operational analysis is conducted, as forces are applied to the repeater, the loose component could impact and damage optical components within the repeater. These forces may not be realized until the repeater is installed under the sea. Thus, whereas a repeater could be functioning as designed when it is operationally analyzed, the repeater could have a previously undiscoverable problem that could affect its operation in the future. Currently, it is not known how to audibly detect this type of defect. Whereas the loose component may generate a noise within the repeater as a result of impacting other components, this noise is not audible with the naked ear because of the thickness of the copper walls of the sealed repeater.

Therefore, it would be desirable to provide an apparatus and method for examining the internal components of a sealed container. This apparatus and method could be utilized to examine sealed containers before they are installed in locations where they may not be easily accessible. Similarly, the apparatus and method could be utilized to examine containers that have been previously installed in difficult to access locations and which are later accessible due to relocation of the container, etc. Thus, the apparatus and method would provide a diagnostic capability that could be utilized at any point in the life cycle of the sealed container.

SUMMARY OF THE INVENTION

In accordance with the present invention, a method and apparatus for examining internal components of a sealed container is provided. In one embodiment, the method includes the steps of attaching an acoustic sensor to an outer surface of the sealed container and moving the sealed container about at least one axis of the sealed container. An audio signal is received from the acoustic sensor, where the audio signal is generated by a component within the sealed container that is put into motion as a result of the step of moving the sealed container about the at least one axis. The audio signal is analyzed to determine the frequency of the signal.

In an embodiment for an apparatus of the present invention, an acoustic sensor is attached to the sealed container. An amplifier is coupled to the acoustic sensor and receives an audio signal from the acoustic sensor. The audio signal is generated by a component within the sealed container that is put into motion as a result of movement of the sealed container. A receiver is coupled to the amplifier and receives the amplified audio signal.

BRIEF DESCRIPTION OF THE DRAWINGS

The various features of the invention will best be appreciated by simultaneous reference to the description which follows and the accompanying drawings, in which.

DETAILED DESCRIPTION

Figure 1:
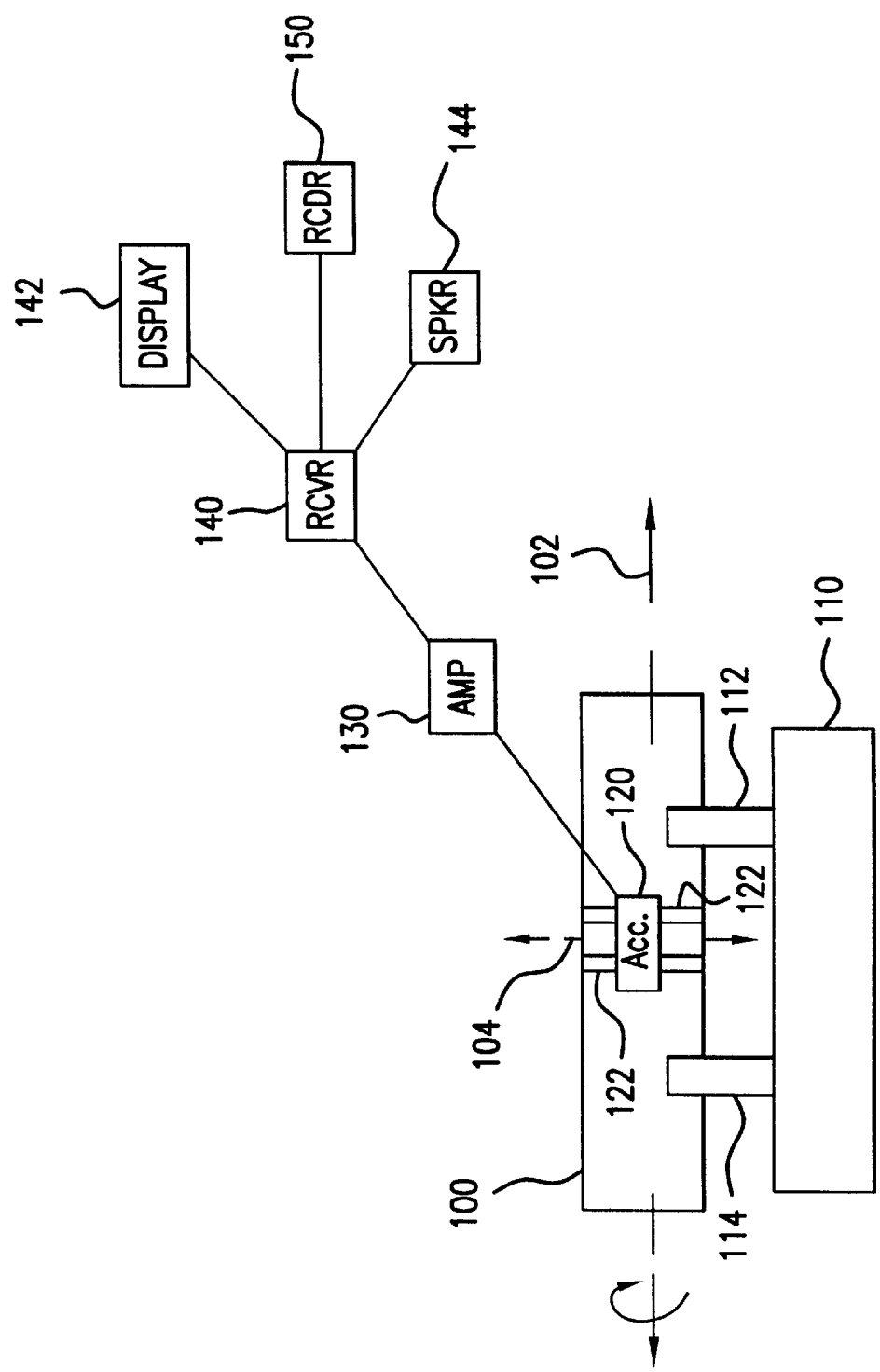
FIG. 1 illustrates an embodiment for an apparatus for examining the internal components of a sealed container in accordance with the principles of the present invention.

FIG. 1 illustrates a first embodiment for an apparatus for examining internal components of a sealed container. As can be seen, and as will be described further below, the embodiment of FIG. 1 includes an acoustic sensor 120, an amplifier 130, a receiver 140, and a recorder 150.

Fiber optic repeater 100 is a hermetically sealed, cylindrical container that contains within it fiber optic components that are capable of regenerating an optical signal that is received within repeater 100. Fiber optic repeater 100 is a component that is utilized in a fiber optic undersea communications system and, as such, is designed to withstand the forces that will be applied to it from the undersea environment. Fiber optic repeater 100 is comprised of approximately one-inch thick beryllium copper and, after the optical components are installed within fiber optic repeater 100, covers are welded onto each end of repeater 100 in order to seal the optical components within repeater 100. Thus, fiber optic repeater 100 is a hermetically sealed container which is comprised of a thick, copper, wall structure. As such, should a component become loose from its mounting structure within repeater 100, it would be impossible to detect the loose component from outside of repeater 100 with the naked ear.

Fiber optic repeater 100 is movably supported within base 110. Base 110 may be configured as any of a variety of structures, however, fiber optic repeater 100 must be able to be moved while it is positioned within base 110. Thus, the present invention may be practiced by either moving base 110 such that fiber optic repeater 100 is moved or may be practiced by supporting fiber optic repeater 100 within base 110 such that the fiber optic repeater 100 may be moved with respect to a stationary base 110. The present invention is not limited to any particular mechanism for resulting in movement of fiber optic repeater 100.

If the present invention were to be practiced by moving base 110 in order to move fiber optic repeater 100, base 110 could be a structure that vibrates on a mounting structure. Alternatively, if the present invention were to be practiced by moving fiber optic repeater 100 within a stationary base 110, support structures 112 and 114 of base 110 could be wheels that are rotatably mounted on base 110 such that fiber optic repeater 100 may be rotated about its longitudinal axis 102 in order to move fiber optic repeater 100. If the vibratory base 110 was utilized as described above, fiber optic repeater 100 could be vibrated about its transverse axis 104. Regardless of how fiber optic repeater 100 is moved, fiber optic repeater 100 is moved such that any component that has loosened from its mounting structure within repeater 100 is caused to impact structure within fiber optic repeater 100 and, consequently, generate a sound within fiber optic repeater 100.

As stated previously, because the wall structure of fiber optic repeater 100 is comprised of thick copper, any sound generated by a loose component within fiber optic repeater 100 as a result of moving repeater 100 would not be audible from outside of repeater 100 by the naked human ear. Therefore, in order to detect any sounds from within fiber optic repeater 100, and consequently the presence of a loose component within fiber optic repeater 100, an acoustic sensor 120 is attached to the outer surface of repeater 100. Acoustic sensor 120 may be any of a variety of different types of devices that are capable of detecting an audio frequency from inside of repeater 100. As such, one embodiment for acoustic sensor 120 may be an accelerometer. Accelerometer 120 would be attached to the outside surface of fiber optic repeater 100 such that any sounds generated within fiber optic repeater 100 would travel through the wall structure of repeater 100 and be detected by acoustic sensor 120.

Acoustic sensor 120 may be attached to fiber optic repeater 100 by any of a variety of methods, such as, for example, by utilizing an adhesive or by magnetically attaching acoustic sensor 120 to fiber optic repeater 100. In order to magnetically attach acoustic sensor 120 to fiber optic repeater 100, a magnet would be attached to acoustic sensor 120. Because the magnet would not attach to the copperwalled repeater 100, metal bands 122 could be strapped around fiber optic repeater 100. The magnet attached to acoustic sensor 120 would attach to the metal bands 122 that are wrapped around fiber optic repeater 100. Thus, acoustic sensor 120 could be indirectly magnetically attached to fiber optic repeater 100.

As described above, when fiber optic repeater 100 is moved on base 110, any loose component within repeater 100 would create a sound within repeater 100 due to the loose component contacting other structure(s) within repeater 100. Acoustic sensor 120 detects the sound made by the loose component and transmits a signal representative of the sound made by the loose component to amplifier 130. Amplifier 130 amplifies the signal and provides the signal to output device, or receiver, 140. Receiver 140 receives the amplified signal and provides an output of the amplified signal such that an operator may analyze the frequency of the sound(s) generated from within repeater 100. Receiver 140 may provide a visual output of the frequency of the received signal on a display 142 or may provide an audible output of the signal on a speaker 144. Regardless of how receiver 140 outputs the received signal from amplifier 130 and acoustic sensor 120, an operator is able to analyze the signal and determine if the frequency of the sound from inside repeater 100 is of interest. Receiver 140 may also provide the received signal to recorder 150 where the signal may be recorded for record or analysis purposes. Recorder 150 may be any of a variety of recording devices including analog recorders or a digital tape recorder. Computers with appropriate sound cards can be used along with analog or digital computers.

Thus, by utilizing the embodiment of FIG. 1 for the present invention, an operator is able to detect a sound from within fiber optic repeater 100 by utilizing an acoustic sensor 120 that is attached to the outside of repeater 100. Any sounds generated from within fiber optic repeater 100 as a result of moving fiber optic repeater 100 on base 110, thus causing a loose component within repeater 100 to contact structure within repeater 100, would be detected by acoustic sensor 120. Acoustic sensor 120 provides a signal to amplifier 130 which amplifies the received signal and provides it to receiver 140. Receiver 140 outputs the frequency of the sound generated within repeater 100 such that an operator is able to analyze the frequency of the generated sound. As such, a loose component within repeater 100 can be detected and analyzed by an operator.

Figure 2:
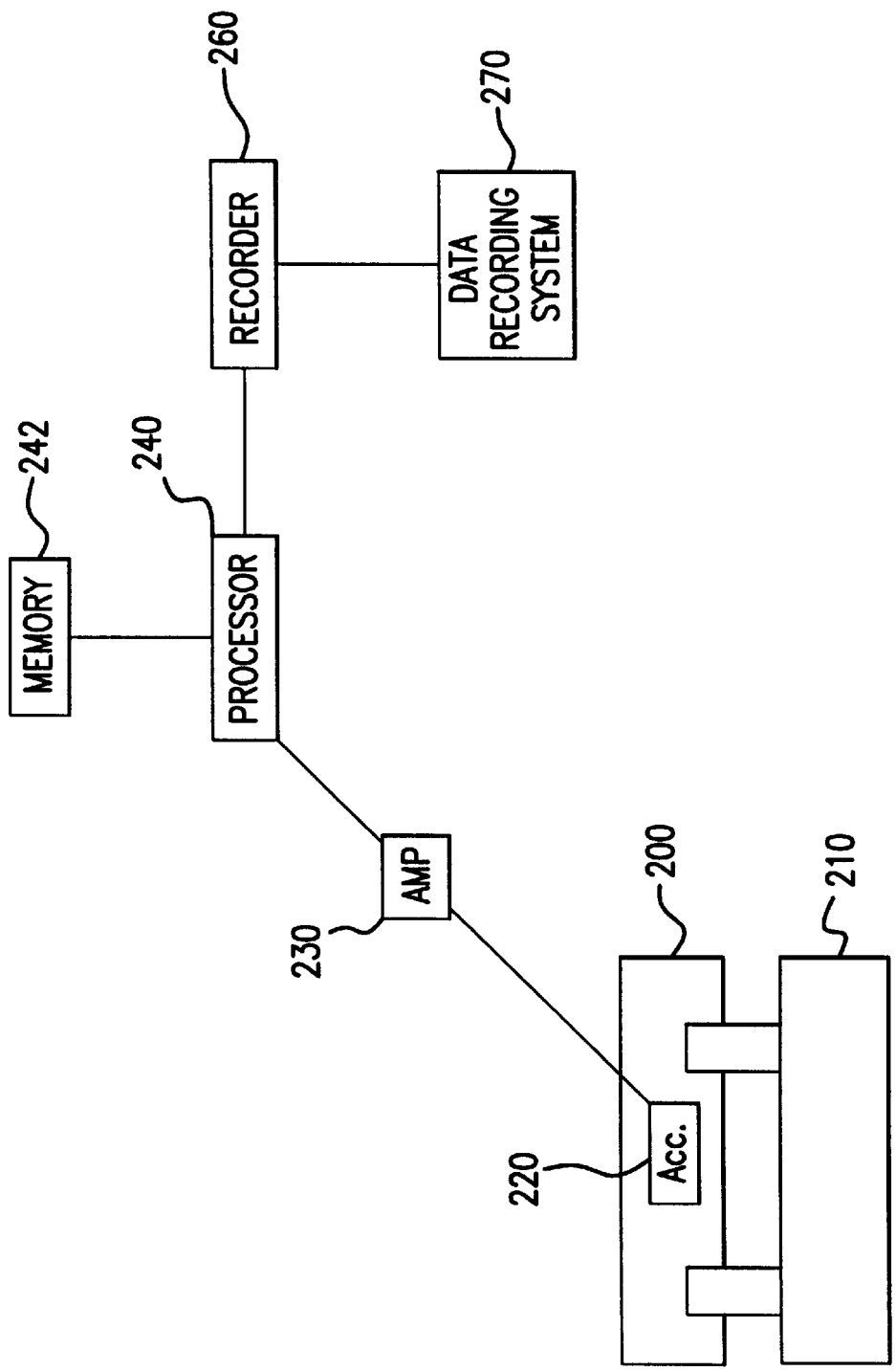
FIG. 2 illustrates a second embodiment for an apparatus for examining the internal components of a sealed container in accordance with the principles of the present invention.

FIG. 2 illustrates an alternative embodiment for the present invention. As can be seen in FIG. 2, fiber optic repeater 200 is also movably supported within base 210. An acoustic sensor 220 is attached to fiber optic repeater 200. Acoustic sensor 220 operates as previously described for the embodiment of FIG. 1 and detects any sounds generated by a loose component within optical repeater 200. Acoustic sensor 220 provides a signal to amplifier 230 where amplifier 230 amplifies the signal and provides it to a processor 240. Whereas the embodiment of FIG. 1 utilizes a receiver 140 to receive the amplified signal from amplifier 130, in the embodiment of FIG. 2 a computer, or processor, 240 receives the amplified signal from amplifier 230.

Memory 242 is coupled to processor 240 and stores within it frequency data for sounds that may be of interest to an operator. This frequency data may be for any of a variety of frequencies, however, frequencies between 8 to 50 kHz have been found to be most representative of the types of sounds that would result from loose components within repeater 200 which are of interest to a user of the present invention. Processor 240 retrieves the stored frequency data from memory 242 and compares the amplified signal received from amplifier 230 to the stored frequency data retrieved from memory 242. If the received signal from amplifier 230 correlates to the frequency data retrieved from memory 242, processor 240 outputs the signal to an operator such that the operator may further analyze the signal.

Processor 240 may output the signal by any of a variety of methods as described previously in connection with the embodiment of FIG. 1, including visually displaying the signal or providing an audio output of the signal. The signal that is output from processor 240 may be recorded on recorder 260, as was also described in connection with the embodiment of FIG. 1. The signal recorded by recorder 260 may be input into a data recording system 270, which may be utilized for any of a variety of purposes including inventory purposes or maintenance purposes. Processor 240 correlates the received signal to data identifying the specific repeater 200 that is being tested and this associated data of the received signal and the particular tested repeater can be stored within data recording system 270. Thus, a record of the test results for the particular repeater may be maintained.

If the signal received by processor 240 from amplifier 230 does not correlate with a frequency retrieved from memory 242, processor 240 will filter out that signal and will not provide data for that signal to an operator since it is not likely that the frequency is of interest to the operator. Thus, whereas the embodiment of FIG. 1 utilizes receiver 140 to output all received signals to an operator, the embodiment of FIG. 2 utilizes a processor 240 to analyze the received signal from amplifier 230 in order to determine whether to output the received signal to the operator.

Figure 3:
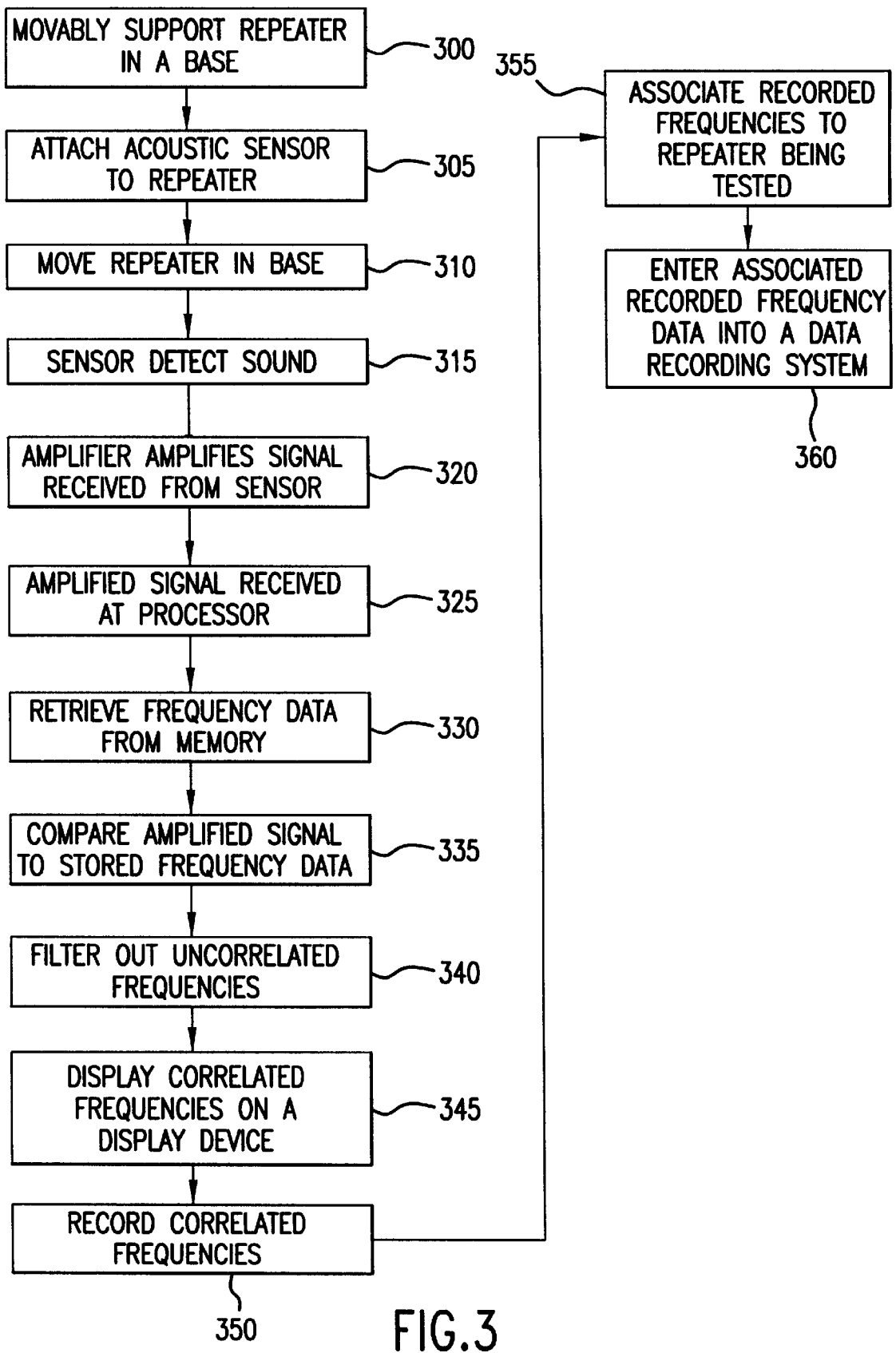
FIG. 3 illustrates a process flow chart for an embodiment of a method of practicing the present invention.

FIG. 3 illustrates the method steps for practicing an embodiment of the present invention. In step 300, a hermetically sealed fiber optic repeater is movably supported within a base. An acoustic sensor, which may be an accelerometer, is attached to an outer surface of the repeater, step 305. In step 310, the repeater is moved within the base. A sound which is generated by a loose component within the fiber optic repeater as a result of moving the repeater is detected by the accelerometer, step 315. The accelerometer provides a signal to an amplifier where the amplifier amplifies the received signal from the accelerometer, step 320. In step 325, the amplified signal is received at a signal processor. The signal processor retrieves stored frequency data from a memory, step 330, and compares the amplified signal received from the amplifier to the retrieved frequency data, step 335. The processor filters out any frequencies in the amplified signal that do not correlate with the retrieved frequency data, step 340. In step 345, frequencies that are correlated to the stored frequency data are displayed on a display device. In step 350, the correlated frequencies are recorded on a recording device and, in step 355, the recorded frequencies are associated with the particular repeater that is being tested. In step 360, the associated recorded frequency data is entered into a data recording system.

The method steps shown in FIG. 3 are not intended to be all inclusive of all of the features of the present invention, as described in the specification. The specification, when read as a whole, fully describes the apparatus and method of the present invention.

As discussed previously, the present invention is not limited to any particular device for an acoustic sensor and a receiver. Any devices which are capable of detecting a sound and outputting the sound for analysis by a user can be utilized. For example, it is contemplated that a stethoscope could be utilized when practicing the present invention. The sensor of the stethoscope could be contacted with the outside surface of the repeater where the sensor would be able to detect any sounds generated within the repeater. The detected sounds would be transmitted by the sensor of the stethoscope to the ear pieces of the stethoscope where a user would be able to hear the sounds generated within the repeater. Thus, a stethoscope could be utilized in a new manner in order to practice a method of the present invention.

Whereas the present invention has been described as being utilized in the context of detecting loose components within a fiber optic repeater, the present invention is not limited to only being practiced in this context. The present invention has utility for detecting loose components within any type of sealed container, including, for example, engine components, entertainment systems, etc.

The disclosed embodiments are illustrative of the various ways in which the present invention may be practiced. Other embodiments can be implemented by those skilled in the art without departing from the spirit and scope of the present invention.

What is claimed is:

1. A method for examining internal components of a sealed fiber optic repeater comprising the steps of:

attaching an acoustic sensor to an outer surface of the sealed repeater;

moving the sealed repeater about at least one of its axis;

receiving an audio signal from said acoustic sensor at a receiver, said audio signal generated by a component within the sealed repeater that is put into motion as a result of said step of moving the sealed repeater about said at least one axis; and analyzing said audio signal.

2. The method of claim 1 further comprising the step of recording said audio signal.

3. The method of claim 2 wherein said audio signal is recorded on a digital tape recorder.

4. The method of claim 2 further comprising the steps of:

associating the audio signal to the sealed repeater; and entering data representative of said associated audio signal into a data recording system.

5. The method of claim 1 further comprising the steps of:

inputting said audio signal into a computer;

retrieving stored frequency data from a storage device; and comparing said audio signal to said stored frequency data to determine if said audio signal matches said stored frequency data.

6. The method of claim 5 further comprising the step of displaying data representative of said audio signal on a display device if said audio signal matches said stored frequency data.

7. The method of claim 5 further comprising the step of recording said audio signal on a recorder if said audio signal matches said stored frequency data.

8. The method of claim 1 further comprising the step of amplifying said audio signal.

9. An apparatus for examining internal components of a sealed fiber optic repeater comprising:

an acoustic sensor, said acoustic sensor attached to said sealed repeater;

an amplifier, said amplifier coupled to said acoustic sensor and amplifying an audio signal received from said acoustic sensor, said audio signal generated by a component within the sealed repeater that is put into motion as a result of movement of the sealed container; and an output device, said output device coupled to said amplifier and receiving said amplified audio signal.

10. The apparatus of claim 9 further comprising:

a metal band, said metal band attached too the sealed repeater; and a magnet, said magnet attached to said acoustic sensor;

wherein said magnet is magnetically attached to said metal band.

11. The apparatus of claim 9 wherein said acoustic sensor is an accelerometer.

12. The apparatus of claim 9 wherein said acoustic sensor is attached to the sealed repeater by an adhesive.

13. The apparatus of claim 9 further comprising:

a memory, said memory storing frequency data and wherein said output device is a processor, said processor coupled to said memory and wherein said processor correlates said audio signal to said stored frequency data.

14. The apparatus of claim 13 wherein said processor associates said audio signal to the sealed repeater and further comprising a data recording system, said data recording system storing said associated audio signal.

15. The apparatus of claim 13 wherein said stored frequency data includes frequencies between 8 and 50 kilohertz.

16. The apparatus of claim 9 further comprising a display device, said display device coupled to said output device and displaying data representative of said audio signal.

17. A diagnostic system comprising:

a base;

a hermetically sealed fiber optic repeater, said repeater movably supported within said base;

an accelerometer, said accelerometer attached to said fiber optic repeater;

an amplifier, said amplifier coupled to said accelerometer; and an acoustic signal receiver, said receiver coupled to said amplifier.

18. The system of claim 17 further comprising a memory, said memory storing frequency data and wherein said acoustic signal receiver includes a processor, said processor coupled to said memory.

19. The system of claim 17 wherein said base includes a plurality of wheels, said plurality of wheels rotatably mounted to said base.

* * * * *